United States Patent [19]

Griffith et al.

[11] 4,317,672
[45] Mar. 2, 1982

[54] METHOD AND PRODUCT FOR TREATING SOIL TO SUPPRESS THE NITRIFICATION OF AMMONIUM NITROGEN THEREIN

[75] Inventors: Jeffrey D. Griffith, Lafayette, Calif.; Thomas M. Ozretich, Vancouver, Wash.

[73] Assignee: The Dow Chemical Company, Midland, Mich.

[21] Appl. No.: 59,086

[22] Filed: Jul. 19, 1979

[51] Int. Cl.³ ............................................ C05G 3/08
[52] U.S. Cl. .................................... 71/27; 71/28; 71/59
[58] Field of Search ................ 71/11, 28, 59, 122, 71/27, 1, 7; 560/254; 260/410.5; 568/812, 811

[56] References Cited

U.S. PATENT DOCUMENTS 3,814,807  6/1974  Fan ........................................ 560/254
4,050,922  9/1977  Markley ................................. 71/122

*Primary Examiner*—William F. Smith
*Attorney, Agent, or Firm*—Merlin B. Davey

[57] ABSTRACT

The present invention relates to crop culture and is particularly concerned with practices for conserving soil nitrogen and for supplying the soil nitrogen requirements for plant nutrition. These practices involve the employment, as active agent, of a novel butane compound having the formula

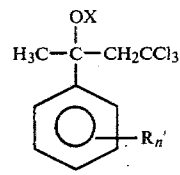

wherein
X is H or

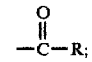

R is H or $C_1$-$C_8$ alkyl;
R' is $C_1$-$C_4$ alkyl, $C_1$-$C_4$ alkoxy or halo and
n is an integer from 0 to 2.

18 Claims, No Drawings

METHOD AND PRODUCT FOR TREATING SOIL TO SUPPRESS THE NITRIFICATION OF AMMONIUM NITROGEN THEREIN

BACKGROUND OF THE INVENTION

The nature of the agricultural problem for which the present invention constitutes a remedy has previously been discussed in the prior art. See, for example, U.S. Pat. Nos. 3,050,380; 3,135,594 and 3,533,774.

The present standard nitrification inhibitor on the market is 2-chloro-6-trichloromethyl pyridine (nitrapyrin). Because of loss by volatilization from treated fertilizers during storage, the use of this compound has tended to be restricted to applications where it can be applied simultaneously with fertilizer, for example, with anhydrous or aqueous ammonia. However, in many parts of the world, fertilizers are applied largely in the solid form, and, in such applications, it is desired to employ a nitrification inhibitor having less volatility and greater persistence.

DESCRIPTION OF THE PRIOR ART

It has been common practice for improving plant nutrition and conserving soil nitrogen to treat plant growth media with a (trichloromethyl)pyridine compound, i.e., a compound having a pyridine nucleus and being substituted thereon by at least one trichloromethyl group as taught in U.S. Pat. No. 3,135,594. Among the suitable compounds are those containing chlorine or methyl substituents on the pyridine nucleus in addition to a trichloromethyl group and are inclusive of chlorination products of methylpyridines such as lutidine, collidine and picoline.

SUMMARY OF THE INVENTION

It has now been found that soil nitrogen may be conserved and plant nutrition improved by treating plant growth media with a novel butane compound of the formula

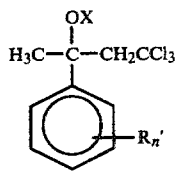

wherein
X is H or

R is H or $C_1$-$C_8$ alkyl;
R' is $C_1$-$C_4$ alkyl, $C_1$-$C_4$ alkoxy or halo and
n is an integer of 0 to 2.

DETAILED DESCRIPTION OF THE INVENTION

By the practice of this invention, the nitrification of ammonium nitrogen in the soil to nitrate nitrogen is suppressed, thereby preventing the rapid loss of ammonium nitrogen from the soil. Furthermore, by proper distribution of the novel butane compound, this action of inhibiting the transformation of ammonium nitrogen to nitrate nitrogen is effective over a prolonged period of time including those situations where treated fertilizer is stored for some time before use. The ammonium nitrogen may arise from added ammonium nitrogen fertilizers or be formed in the soil by conversion of the organic nitrogen constituents found in soil or added thereto as components of organic fertilizers.

The provision of an effective but sublethal dosage of the butane compound in the soil or growth medium is essential for the practice of the present invention. In general, good results are obtained when the growth medium is impregnated with the butane compound in the amount of from about 0.05 part to about 4000 parts or more by weight per million parts by weight of growth medium. (Hereinafter, the abbreviation ppm when employed is meant to designate parts by weight of butane compound per million parts by weight of soil or growth medium.) The preferred amounts to be employed are dependent upon the particular situation. Thus, in determining the amount to be employed, consideration is made not only of the treatment need, i.e., soil pH, temperature, soil type, etc. but also of the mode of application to soil. When the butane compound is to be applied in a broadcast application, the concentration may frequently be less than in row or band application where for a substantial depth and width within the vicinity of application there may be a very high concentration of the butane compound. When application is made near the root zone of growing plants or when application is made immediately prior to seeding or transplanting, the amounts supplied are frequently at a lower rate than when application is made at the end of the growing season to prepare the soil for the following season. By dispersing very large dosages in growth media, a prolonged inhibition of nitrification may be obtained over a period of many months. The concentration of the active butane compound is eventually reduced to a minimum by decomposition in the soil.

In one method for carrying out the present invention, the butane compound is distributed throughout the growth media in a broadcast application such as by spraying, dusting, distributing in irrigation water, etc. In such application, the butane compound is supplied in amounts sufficient to permeate the growing area of soil with an amount of from about 0.05 to about 1000 ppm. In field administration, the butane compound may be distributed in the soil in the amount of at least 0.05 pound per acre and through such cross-section of the soil as to provide for the presence therein of an effective concentration of the agent. It is usually preferred that the butane compound is distributed to a depth of at least two inches below the soil surface and at a dosage of at least 0.1 pound per acre.

In another method for carrying out the present invention, the butane compound is administered to the growth medium in a band or row application. In such application, administration is made with or without carrier in amount sufficient to supply to soil or growth medium a concentration of the butane compound which may be as high as 4000 ppm or more. After administration with or without discing or dragging, subsequent irrigation or rainfall distributes the butane compound throughout the growth medium.

In one embodiment of the present invention, the butane compound is distributed throughout the growth media prior to seeding or transplanting the desired crop plant.

In another embodiment, the soil in the root zone of growing plants is treated with the butane compound in an amount effective to inhibit nitrification. Oftentimes it is desirable to treat the soil adjacent to plants, and this procedure may be carried out conveniently in side-dressing operations.

In a further embodiment, soil may be treated with the compounds following harvest or after fallowing to prevent rapid loss of ammonium nitrogen and to build up the ammonium nitrogen formed by conversion of organic nitrogen compounds. Such practice conserves the soil nitrogen for the following growing season. In such application, the upper limit is primarily an economic consideration.

In an additional embodiment, the soil is treated with the butane compound in conjunction with the application of reduced nitrogen fertilizers. The treatment with the butane compound may be carried out prior to, subsequent to or simultaneously with the application of fertilizers. Such practice prevents the rapid loss of the ammonium nitrogen added as fertilizer and of the ammonium nitrogen formed from organic nitrogen in fertilizers by the action of soil microorganisms. The administration to the soil of the butane compound in an ammonium nitrogen or ammonium nitrogen forming fertilizer composition constitutes a preferred embodiment of the present invention.

The present invention may be carried out by distributing the butane in an unmodified form through growth medium. The present method also embraces distributing the compound as a constituent in liquid or finely divided solid compositions. In such practice, the butane compound may be modified with one or more additaments or soil treating adjuvants including water, petroleum distillates or other liquid carriers, surface-active dispersing agents, finely divided inert solids and nitrogen fertilizers. Depending upon the concentration of the butane compound, such augmented composition may be distributed in the soil without further modification or be considered a concentrate and subsequently diluted with additional inert carrier to produce the ultimate treating composition. The required amount of the butane compound may be supplied to growth media in from 1 to 50 gallons of organic solvent carrier, in from 5 to 27,000 or more gallons of aqueous carrier or in from about 20 to 2,000 pounds of solid carrier per acre treated. When an organic solvent carrier is employed, it may be further dispersed in the above volume of aqueous liquid carrier.

The concentration of the butane compound in compositions to be employed for the treatment of growth media is not critical and may vary considerably provided the required dosage of effective agent is supplied to the growth media. The concentration of the butane compound may vary from about 0.00001 percent by weight to about 95 percent by weight of the composition, depending on whether the composition is a treating composition or a concentrate composition and whether it is in the form of a solid or a liquid. In aqueous liquid treating compositions, concentrations of from about 0.00001 percent to about 0.25 percent by weight of the butane compound is considered the preferred composition. The concentration of the butane compound in organic solvents may be from about 2 to about 95 percent by weight. Concentrate liquid compositions generally contain from about 2.5 to about 95 percent by weight of the butane compound. Treating compositions generally contain from about 0.0001 percent to about 10 percent by weight of the butane compound. Concentrate compositions contain from about 2.5 to about 95 percent of the butane compound.

Liquid compositions containing the desired amount of the butane compound may be prepared by dispersing the latter in one or more liquid carriers such as water or an organic solvent, with or without the aid of a suitable surface-active dispersing agent or emulsifying agent. Suitable organic solvents include acetone, diisobutylketone, methanol, ethanol, isopropyl alcohol, toluene, methylene chloride, chlorobenzene and the petroleum distillates. The preferred organic solvents are those which are of such volatility that they leave little permanent residue in the soil. When the solutions of the butane compound in organic solvents are to be further diluted to produce aqueous dispersions, the preferred solvents include acetone and the alcohols. When the liquid carrier is entirely organic in nature, particularly desirable carriers are the petroleum distillates boiling almost entirely under 400° F. at atmospheric pressure and having a flash point above about 100° F. Dispersing and emulsifying agents which may be employed in liquid compositions include condensation products of alkylene oxides with phenols and organic acids, alkyl aryl sulfonates, polyoxyalkylene derivatives of sorbitan esters, complex ether alcohols, mahogany soaps and the like. The surface-active agents are generally employed in the amount of from 1 to 20 percent by weight of the butane compound.

Solid compositions containing the active butane compound may be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with the butane compound or wet with a solution or dispersion thereof in a volatile organic solvent. Depending upon the proportions of ingredients, these compositions may be employed without further modification or be considered concentrates and subsequently further diluted with solid surface-active dispersing agent, talc, chalk, gypsum, or the like to obtain the desired treating composition. Furthermore, such concentrate compositions have the properties of wettable powders and may be dispersed in water with or without added dispersing agent or agents to prepare aqueous soil treating compositions.

Soil treatment compositions may be prepared by dispersing the butane compound in fertilizers such as ammonium fertilizer or organic nitrogen fertilizer. The resulting fertilizer composition may be employed as such or may be modified as by dilution with additional nitrogen fertilizer or with inert solid carrier to obtain a composition containing the desired amount of active agent for treatment of soil. Further, an aqueous dispersion of the butane compound-fertilizer composition may be prepared and administered to the growth medium. Fertilizer compositions comprising the butane compound in intimate admixture with ammonium fertilizers constitute preferred embodiments of the present invention.

In fertilizer compositions comprising a reduced nitrogen fertilizer, it is desirable that the butane compound be present in an amount of at least about 0.05 percent by weight based on the weight of the nitrogen present in the fertilizer as reduced nitrogen and may be present in amounts as high as 95 percent by weight of the reduced nitrogen in the fertilizer. Thus, when a fertilizer composition contains both reduced nitrogen and other forms of nitrogen such as in the case of ammonium nitrate fertilizer compositions, the amount of butane compound is based on the weight of nitrogen present in the ammonium component.

In operations carried out in accordance with the present invention, the soil may be treated in any convenient fashion with the active compound or a composition containing the latter. For example, these modified or unmodified compositions may be mechanically mixed with the soil; applied to the surface of soil and thereafter dragged or disced into the soil to a desired depth; or transported into the soil with a liquid carrier such as by injection, spraying or irrigation. When the distribution is carried out by introducing the compound in the water employed to irrigate the soil, the amount of water is varied in accordance with the moisture content of the soil in order to obtain a distribution of the compound to the desired depth. The compound may be readily and conveniently distributed to a depth of a few inches to four feet by irrigation methods. The preferred methods embrace procedures using any of these steps or combination of steps wherein the compound is distributed in the soil substantially simultaneously with a reduced nitrogen fertilizer.

The following examples illustrate the invention but are not to be construed as limiting. In the following examples melting points were determined on a Thomas-Hoover capillary melting apparatus and are corrected. IR spectra were recorded on a Beckman AccuLab 3 and NMR spectra on a Varian Associates EM-360 instrument (Me$_4$Si) and are in accord with proposed structures. Preparative liquid chromatography was carried out on a Waters Associates Prep LC/System 500 using their PrePak-500/Silica columns. Refractive index measurements were recorded on a Bausch and Lomb instrument fitted with a Brinkman Lauda K-2/R temperature control. Experimental details are given for one member of each class of compounds; other members were prepared in an analogous manner. The yields reported are from reactions carried out only once, and do not represent maximum possible yields.

EXAMPLE 1

Preparation of α-(2,2,2-Trichloroethyl) phenyl Oxirane

Into a stirred, refluxing solution of 68 g (0.3 mole) of 85% m-chloroperbenzoic acid in 400 ml of chloroform was added, in a slow stream, 78 g (0.3 mole) of α-(2,2,2-trichloroethyl)styrene in 300 ml of chloroform. After 2 hours the chloroform was allowed to cool and the solid m-chlorobenzoic acid was filtered off. The solution was then washed with two 500-ml portions of 3% aqueous caustic. The organic phase was dried over Na$_2$SO$_4$, filtered and concentrated in vacuo to give 80 g of yellowish oil, (which solidified upon standing). Recrystallization (hexane) gave 65 g (78%) of white needles, m.p. 60°–61.5° C.

EXAMPLE 2

Preparation of α-Methyl-α-(2,2,2-Trichloroethyl)Benzyl Alcohol

To a slurry of 3.8 g (0.1 mole) of lithium aluminum hydride (95%) in 300 ml of ether was added slowly (T<30° C.) 50 g (0.2 mole) of α-(2,2,2-trichloroethyl)-phenyl oxirane in 150 ml of ether. After 20 minutes, 3.8 ml of water was added dropwise, followed by 3.8 g of 15% aqueous caustic, then 11.4 ml of water. After an hour of stirring, the white inorganic residue was filtered off. The ether was dried over Na$_2$SO$_4$, filtered and concentrated in vacuo to give 46 g (91%) of colorless oil shown to be 96% pure by gas chromatography. (No impurities detectable by NMR.) See Table I, Compound 1 for activity.

EXAMPLE 3

Preparation of Benzenemethanol: α-Methyl-α-(2,2,2-Trichloroethyl)-, Acetate

To an 80°–90° C. solution of 36 g (0.3 mole) of N,N-dimethylaniline and 25 g (0.1 mole) of α-methyl-α-(2,2,2-trichloroethyl)benzylalcohol was added over a 5 minute period 23.1 g (0.3 mole) of acetyl chloride. After about 4 hours the solution was allowed to cool to 40°–50° C. when excess water was added dropwise until excess acetyl chloride was reacted. (Temperature was not allowed to exceed 90° C.) Then the solution was partitioned between 250 ml of 3 N HCl and 150 ml hexane. The organic phase was washed with two 150-ml portions of 3 N HCl, then with two 150-ml portions of 5% aqueous caustic, and two times with water. The organic phase was dried over Na$_2$SO$_4$, filtered and concentrated in vacuo to give 26.5 g (90%) of desired ester. Gas chromatography showed 92% purity. See Table I, Compound 2 for activity.

EXAMPLE 4

Preparation of Benzenemethanol: α-Methyl-α-(2,2,2-Trichloroethyl)-, formate

A solution of 20 g (0.073 mole) of α-methyl-α-(2,2,2-trichloroethyl)benzyl chloride in 20 ml tetrahydrofuran was added to a solution of 20 g (0.3 mole) sodium formate in 25 ml of 98% formic acid. After about 4 hours the organics were extracted with two 150-ml portions of hexane. The hexane layer was washed once with 0.5 M Na$_2$CO$_3$, dried over Na$_2$SO$_4$, filtered and concentrated. The resultant oil was shown by gas chromatography (gc) analysis to be 40–50% desired formate with 35–40% α-(2,2,2-trichloroethyl)styrene and 10–15% α-methyl-α-(2,2,2-trichloroethyl)benzyl alcohol. The formate could be separated in pure form by preparative liquid chromatography using 5% acetone in hexane as the eluant.

Anal. Calcd for C$_{11}$H$_{11}$Cl$_3$O$_2$: C, 46.92; H, 3.94. Found: C, 46.73; H, 4.00.

See Table I, Compound 17 for activity.

Employing the above procedures a number of novel compounds have been prepared as indicated in the following Table I. A number of these compounds were tested for their ability to reduce the rate of nitrification of ammonium nitrogen, applied as urea to soil. Their activity, relative to the standard 2-chloro-6-trichloromethylpyridine, is also reported in the table.

The test method comprised selecting a soil which had a low nitrate concentration and good nitrification activity. A sufficient volume of water was added to 50 g of the soil in a wide-mouth, screw-cap, 240-ml, glass bottle, such that the moisture content of the mixture was made equal to the ⅓ bar tension value for that soil. The mixture was thoroughly stirred with a spatula before sealing. The added water contained 10 mg (200 ppm) of nitrogen in the form of urea (21.4 mg of urea) and 100 μg (2 ppm based on dry soil weight) of test chemical. When the test chemical had a low water solubility, it was compounded in acetone (or other suitable solvent) in such a way that the final mixture in the soil contained no more than 10 μl of acetone. Acetone slows the rate of soil nitrification and its concentration must be carefully controlled. Single samples of each test chemical were incubated for 2 weeks at 21° C.

The experiment comprised the following types of samples:
1. Nitrate blank containing soil, water and solvent only.
2. Nitrogen standard containing soil, water, urea and solvent, in duplicate and values averaged.
3. Chemical standard containing soil, water, urea, solvent, and nitrapyrin as the standard for comparison, in duplicate, and values averaged.
4. Test chemicals containing soil, water, urea, solvent, and test chemical. Single samples.

The soil samples were analyzed as follows: Sufficient saturated calcium sulfate solution was added to the sample, such that the total volume of added water was 100 ml (included water added during sample preparation). The capped mixture was shaken 10 minutes to solubilize nitrate, the soil particulates were allowed to settle, and the calcium sulfate solution was decanted. The nitrate concentration in the water phase was determined with a nitrate-specific ion electrode such as Orion Model 93-07.

The non-nitrate nitrogen remaining in the soil after 2 weeks (performance value) was calculated as follows:

Percent non-nitrate N remaining in soil =

$$\left[\frac{200\ ppm - \frac{(\text{Sample nitrate N ppm} - \text{soil blank nitrate N ppm}) \times 100\ ml}{50\ g}}{200\ ppm}\right] \times 100.\ =$$

$100 - (\text{Sample nitrate N ppm} - \text{soil blank nitrate N ppm}).$

The performance value for each sample in the experiment was converted to a net performance value by subtracting the average performance value of the solvent-soil check replicates (No. 2 above).

An activity ratio (or percent) was calculated for each test chemical as follows:

$$\frac{\text{Net performance value of test chemical}}{\text{Net performance value of nitrapyrin}} = \text{Activity ratio.}$$

TABLE I

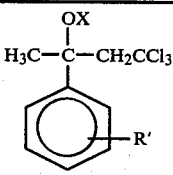

| Compound | X | R' | Refractive Index or BP | % Purity | % Yield | Activity (2 ppm) |
|---|---|---|---|---|---|---|
| 1 | H | — | 73–75 @ .4 mm | 95 | | 98 |
| 2 | Ac | — | 112 @ .3 mm | 92 | | 92 |
| 3 | O=CC$_2$H$_5$ | — | 41–43° mp | 95 | | 88 |
| 4 | O=CC$_3$H$_7$ | — | Not measured | 93 | | 93 |
| 5 | H | 4-Cl | 115 @ .2 mm | 90 | | 98 |
| 6 | H | 3,5-Cl$_2$ | 138 @ | 90 | | 29 |

TABLE I-continued

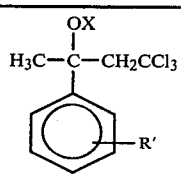

| Compound | X | R' | Refractive Index or BP | % Purity | % Yield | Activity (2 ppm) |
|---|---|---|---|---|---|---|
| 7 | H | 3-Cl | 1.5570 .4 mm | 95 | 30 | 90 |
| 8 | Ac | 3-Cl | 1.5337 | 92 | 73 | 90 |
| 9 | O=CC$_2$H$_5$ | 3-Cl | 1.5260 | 90 | 75 | 78 |
| 10 | H | 3-CH$_3$ | 1.5420 | 95 | 50 | 102 |
| 11 | Ac | 3-CH$_3$ | 1.5280 | 92 | 83 | 100 |
| 12 | H | 3-C$_2$H$_5$ | 1.5394 | 95 | 70 | 84 |
| 13 | Ac | 3-C$_2$H$_5$ | 1.5166 | 95 | 62 | 107 |
| 14 | H | 4-CH$_3$ | 1.5443 | 95 | 55 | 97 |
| 15 | H | 3-OCH$_3$ | 1.5468 | 100 | 30 | 102 |
| 16 | Ac | 3-OCH$_3$ | 1.5315 | 92 | 95 | 97 |
| 17 | O=CH | — | 1.5368 | 99 | 48 | 97 |
| 18 | O=CH | 4-CH$_3$ | 1.5266 | 99 | 4 | 90 |
| 19 | O=CC$_7$H$_{15}$ | — | 1.4958 | 95 | 5 | 111 |
| 20 | H | 3,5-(CH$_3$)$_2$ | 1.5320 | 99 | 75 | 91 |
| 21 | Ac | 3,5-(CH$_3$)$_2$ | 1.5285 | 100 | 60 | 74 |

EXAMPLE 5

α-Methyl-α-(2,2,2-trichloroethyl)benzyl acetate was applied to urea fertilizer and put into 5-gallon pails which were sealed until use. Nitrapyrin was added to 5-gallon pails containing 30 lbs urea immediately before application to the crop. Both chemicals were added as methylene chloride solutions and blended with the fertilizer for uniformity. The pails were sealed when not in use.

The soil was an Indio California sandy loam with 0.5% organic matter and a pH of 7.5 to 8.0. The field was bedded on 36-in. (91 cm) centers and seeded to sweet corn (cv. Quick Silver var. 1116) one day before application of fertilizer treatments. In late winter the fertilizer was applied using a modified Gandy granule applicator. The fertilizer was placed 8 inches each side of and 6 inches below the seed line. One hundred fifty pounds of N per acre (168 kg/Ha) as urea was applied to all plots. The plots were four rows wide by 44 feet (14 meters) long. Four replications were used.

The soil was moist when the fertilizer was applied. A light irrigation was applied within a week after application and the field was irrigated approximately weekly after that.

A visual rating of crop plant growth and color was made 44 days after seeding, when the plants were about 24 inches (0.6 m) tall.

The center two rows of each plot were harvested by hand 85 days after seeding. All ears were picked and graded into "marketable" and "cull" classifications with size as the criterion. After grading, the ears in each category were counted and weighed. After harvest, the leaf above the top ear leaf was sampled (25 leaves per plot), dried, and analyzed for total nitrogen content.

The results are set out in Table II.

TABLE II

| Effect of Test Compound and Nitrapyrin on Yield and Leaf Nitrogen Content of Sweet Corn | | | | | |
|---|---|---|---|---|---|
| Treatments | | | Yield | | Leaf Nitrogen |
| | | | Marketable Ears | Total Ears | |
| Chemical | lbs/A | kg/ha | #/plot | lbs/plot | lbs/plot | % |
| Compound 2, Table I | 1.50 | 1.68 | 109 | 79 | 115 | 2.90 |
| " | 0.75 | 0.84 | 96 | 70 | 102 | 2.86 |
| " | 0.38 | 0.42 | 82 | 57 | 95 | 2.83 |
| Nitrapyrin | 1.50 | 1.68 | 102 | 70 | 104 | 2.70 |
| " | 0.75 | 0.84 | 102 | 70 | 99 | 2.69 |
| " | 0.38 | 0.42 | 88 | 64 | 93 | 2.56 |
| Untreated | — | — | 80 | 57 | 85 | 2.50 |

Sampled area = 2 rows × 44-ft long - 264 ft² - 0.006A.

In the observations made 44 days after seeding, about mid-season, slightly better color and growth were noted in each of the plots with treated fertilizer. At that time, the plants in the substituted benzyl acetate-treated plots appeared slightly larger and greener than those treated with nitrapyrin.

At harvest 85 days after seeding, marked growth and color differences favoring the substituted benzyl acetate were observed. On each basis of measurement used (numbers and weights of marketable ears, total weights of ears (marketable+cull), and nitrogen content of leaves), the treated urea was more effective than untreated urea. The data also show that the substituted benzyl acetate was more efficacious than nitrapyrin for this use.

What is claimed is:

1. A fertilizer composition useful for suppressing the nitrification of ammonium nitrogen in growth media and for preventing rapid loss of ammonium nitrogen therefrom comprising a reduced nitrogen fertilizer and from 0.05 to 95 percent by weight of the reduced nitrogen in the fertilizer of a compound having the formula

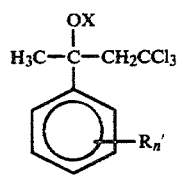

wherein
X is H or

R is H or C$_1$-C$_8$ alkyl;
R' is C$_1$-C$_4$ alkyl, C$_1$-C$_4$ alkoxy or halo and
n is an integer from 0 to 2.

2. Composition of claim 1 where X is H and n is 0.
3. Composition of claim 1 where X is

and n is 0.

4. Composition of claim 3 where R is —CH$_3$.
5. Composition of claim 3 where R is H.
6. Composition of claim 1 where X is H, R' is 3—CH$_3$ and n is 1.

7. Composition of claim 1 where X is

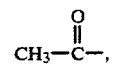

R' is 3—CH$_3$ and n is 1.

8. Composition of claim 1 where X is H, R' is 3—OCH$_3$ and n is 1.

9. Composition of claim 1 where X is

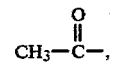

R' is 3—OCH$_3$ and n is 1.

10. A method for suppressing the nitrification of ammonium nitrogen in growth media which comprises impregnating said growth media with a reduced nitrogen fertilizer and from about 0.05 to about 4000 ppm, based on growth media, of a compound having the formula

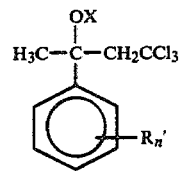

wherein X is H or

where R is H or C$_1$-C$_8$ alkyl;
R' is C$_1$-C$_4$ alkyl, C$_1$-C$_4$ alkoxy or halo and
n is an integer from 0 to 2.

11. Method of claim 10 where X is H and n is 0.
12. Method of claim 10 where X is

and n is 0.

13. Method of claim 12 where R is —CH$_3$.
14. Method of claim 12 where R is H.
15. Method of claim 10 where X is H, R' is 3—CH$_3$ and n is 1.
16. Method of claim 10 where X is

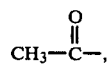
R' is 3—CH$_3$ and n is 1.
17. Method of claim 10 where X is H, R' is 3—OCH$_3$ and n is 1.
18. Method of claim 10 where X is
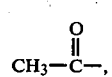
R' is 3—OCH$_3$ and n is 1.
* * * * *